United States Patent [19]

Byers et al.

[11] Patent Number: 4,837,049

[45] Date of Patent: Jun. 6, 1989

[54] METHOD OF MAKING AN ELECTRODE ARRAY

[75] Inventors: Charles L. Byers; Joseph H. Schulman, both of Granada Hills; David I. Whitmoyer, Los Angeles, all of Calif.

[73] Assignee: Alfred E. Mann Foundation for Scientific Research, Sylmar, Calif.

[21] Appl. No.: 875,334

[22] Filed: Jun. 17, 1986

[51] Int. Cl.⁴ .............................................. B05D 5/12
[52] U.S. Cl. ................................... 427/96; 128/642; 128/784; 29/829; 427/79
[58] Field of Search ............................... 128/639–642, 128/644, 784, 802; 427/96, 99; 29/829

[56] References Cited

U.S. PATENT DOCUMENTS

| B 453,031 | 8/1973 | Fukase et al. | 156/3 |
|---|---|---|---|
| 3,755,704 | 8/1973 | Spindt et al. | 313/309 |
| 4,016,886 | 4/1977 | Doss et al. | 128/784 |
| 4,350,164 | 9/1982 | Allaim, Jr. | 128/639 |
| 4,513,308 | 4/1985 | Greene et al. | 357/55 |
| 4,551,149 | 11/1985 | Sciarra | 623/4 |

FOREIGN PATENT DOCUMENTS

| 2555281 | 6/1977 | Fed. Rep. of Germany | 128/639 |
|---|---|---|---|
| 665890 | 6/1979 | U.S.S.R. | 128/642 |

OTHER PUBLICATIONS

Guyton et al, "Theory . . . Chromic Stimulation", Med. & Biol. Eng., vol. 12, No. 5, Sep. 1974, pp. 613-620.
Wise et al, "A Low-Capacitance Multielectrode . . . ", IEEE Trans. BioMed. Eng., vol. 22, No. 3, pp. 212-219, May 1975.
Klomp et al, "Fabrication of Large Arrays . . . ", J. Bio. Material Res., vol. 11, pp. 347-364, 1977.
White, "Integrated Circuits . . . Arrays", 1st Int. Conf. on Elect. Stim. . . . pp. 199-207, 1974.
Spindt et al., "Physical Properties . . . Cones", J. App. Phys., vol. 47, No. 12, pp. 5248 et seq., Dec. 1976.
Prohaska et al., "A 16-Fold Semi-Microelectrode . . . ", Electroenceph & Clin. News, 1979, 47, pp. 629-631.
Wise et al, "An Integrated Circuit . . . ", IEEE Trans. BioMed. Eng., p. 238 et seq., vol. BME17, No. 3, Jul. 1970.
"Multichannel Multiplexed . . . Arrays", Neural Prothesis Program, Un. of Mich., Oct. 1983.
American J. of Physiology, 212 (5), pp. 1209-1214 (1967), P. V. Malven et al.
Brain Research, 142, pp. 363-367 (1978), H. F. Carrer et al.
Ko, "Solid-State . . . Research", IEEE Trans. Oil Bio-Med. Eng., pp. 153-160, vol. 3, No. 2, Feb. 1986.

Primary Examiner—Lee S. Cohen

[57] ABSTRACT

A very small electrode array is disclosed, having numerous, small, sharp, conductive protuberances (needles) which penetrate nerves, organs, muscle or other body part for sensing the electrical activity therein or to provide electrical stimulation. The protuberances are carried on a base and there is included electrical conductors connecting the protuberances to terminals, such as bonding pads, for connection to other electrical circuits. Thus, a method of connecting to living tissue is disclosed. Also, a method of manufacture of an electrode array and associated circuitry is disclosed.

2 Claims, 7 Drawing Sheets

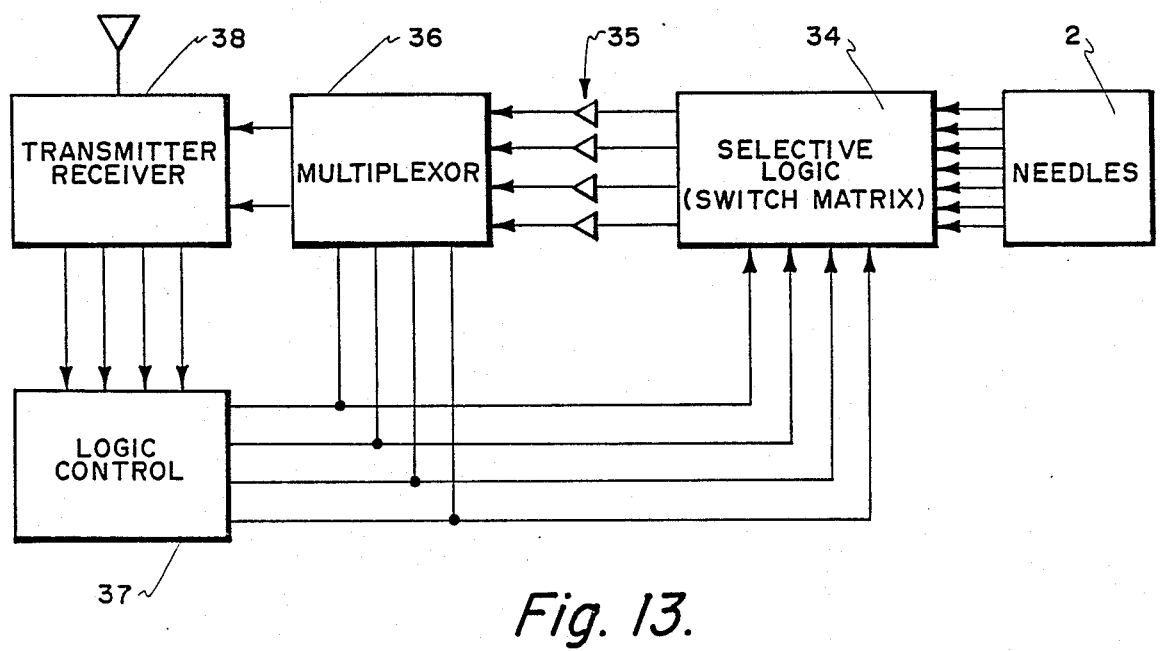
Fig. 12.
Fig. 13.
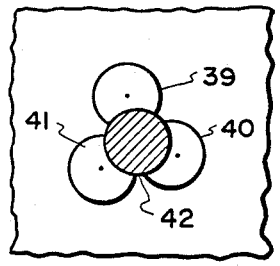
Fig. 14.
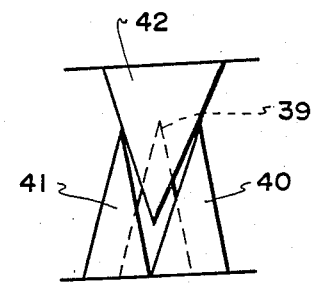
Fig. 15.

METHOD OF MAKING AN ELECTRODE ARRAY

This invention is an array of electrodes for use in obtaining electrical signals from or providing electrical signals to, a living body, ordinarily a human body, and utilizing electrical signals to stimulate or sense, in order to provide treatment of a disorder, to evoke a desired response or effect in a patient or used as a diagnostic tool or monitoring device of normal or abnormal functions. Such treatment, of course, includes improvement of a functional disorder, say, for example, providing, or causing, motion by coordinated neuro-muscular stimulation. Still other uses may be readily found for such an array.

This invention includes also the methods of manufacturing such electrodes and the use of such electrodes in connecting to a living body.

The array of electrodes might well be part of a sensory system and be implanted in a human body, connected to a nerve, or to an organ (the brain or other body organ) or to any other element of the body having electrical activity.

On the other hand, such array of electrodes might be part of a stimulating system for a human body or other animal body, connected to any "excitable tissue", such as a nerve, a muscle, an organ, or any other element of the body responding, or evoking a response, to electrical signals.

BACKGROUND OF THE INVENTION

Information is transmitted in the human body by the nervous system, which correlates and integrates various bodily processes, reactions and adjustments. Electrical pulses travel along the extension (axon) of a nerve cell, from one nerve cell to another, establishing functional pathways to make up the nervous system of the body. Thus, a function of a nerve is to take electric signals from various sources to the receiving locations within the body.

The electrode array may be used anywhere in a nervous system, at the end organs, (for example, without limitation, brain, kidney, liver, stomach, muscle or other tissue), or along the nerve (afferent or efferent) pathways in between.

SENSING

Sensory nerves in the body provide information as to the various bodily conditions, processes, reactions and adjustments. Such information, is in the form of electrical signals and may be monitored (by neurosensing) using appropriate electrical, or electronic, equipment. Electrical activity may be sensed in body elements in order to arrive at a desired treatment of, or to detect, a disorder. Having sensed a particular condition (by the particular electrical activity), various modes of treatment may be provided—administration of medicine, application of electrical signals, or other management and care of the patient.

STIMULATING

Certain nerves in the body direct muscular action and by electrically stimulating an appropriate nerve (neurostimulation), muscular action can be effected. In some cases, the muscle (as well as other organs or excitable tissue) may be directly or indirectly stimulated, in order to treat a disorder. Such treatment may include providing a number of coordinated, stimulation signals to various parts of the muscle or the body. "Stimulation" may mean, in connection with the muscles, the providing of signals which cause motion or movement of the muscles. "Stimulation" in connection with the brain may result in a physical response or it may result in a sensory response (such as vision, feeling, smell, etc.), which involves the senses rather than a physical motion. "Tissue" as used herein is intended to mean any body tissue, nerve, muscle, organ, (including the brain and the spinal cord), or other body part. "Excitable tissue" means tissue to which may be sent electrical signals in order to evoke a response of some kind, including a resulting beneficial effect on or treatment of the patient.

Both of the above concepts, sensing and stimulating, raise the problem as to how to connect to the desired body part, whether it be nerve, muscle, organ, or otherwise. For example, there are usually thousands of fibers in a nerve, and each fiber may be carrying a unique signal. Consequently, problems arise as to how to connect to the desired location on, or within, the selected nerve, in order to sense signals from, or provide signals to, individual fibers. Because of the involvement of electrical signals in both sensing and stimulating, the problem of deriving suitable electrodes for sensing or stimulating has many similarities.

PRIOR ART

The prior art has utilized multiple electrodes. One type of multiple electrode device is illustrated in an article entitled "Integrated Circuits and Multiple Electrode Arrays," by Robert L. White, in Proceedings of the First International Conference on Electrical Stimulation of the Acoustic Nerve as a Treatment . . .", published by Velo-Bind, Incorporated, 1974, pages 199 and following. In that article is shown a needle of 250 micrometers (0.25 millimeters) width, tapered to a point, and having gold leads, of 15 micrometers width, thereon (covered with silicon dioxide). Each gold lead, at its end, near the point of the needle, connects to a flat, circular electrode of approximately 50 micrometers in diameter.

Another type of multiple electrodes is illustrated by an article entitled, "Solid-State Physical Transducers for Biomedical Research," by Wen H. Ko, in IEEE Transactions on Biomedical Engineering, Vol. BME-33, No. 2, February, 1986, pages 153 and following. In that article is shown an electrode having three, sharp-tipped, gold electrodes, (each 1 to 3 micrometers wide), mounted on a silicon carrier and used for sensing skin or tissue.

Current techniques for connecting to nerves also involve nerve cuffs, which are placed around the nerve, and which can only stimulate large numbers of fibers within the nerve.

Also, multiple needles (electrodes) have been individually inserted into tissue to make contact in a localized area of tissue.

BRIEF DESCRIPTION OF THE INVENTION

This invention provides an array of numerous small, sharp, conductive, penetrating protuberances, (needles, or spikes,) of which, a few or many (but certainly some) will make effective electrical contact with the appropriate tissue when the array is applied to a body part. The array, which might be described as a "bed of nails", having dimensions of a few millimeters, is thus adapted to be disposed in a desired location in or on the body. The array includes electrical conductors which connect the protuberances to terminals in order to provide a means for connecting to other electrical circuits. When used in connection with a nerve, or a fiber thereof, the array may be implanted and might be fastened to, around, or in the nerve, with the numerous needles penetrating into the nerve and individual needles making electrical contact with individual nerve fibers.

If the array is used for sensing purposes, the terminals would provide the output signals which would, ordinarily, be amplified and processed to obtain the desired information.

If the array is used for stimulating purposes, the terminals would provide the location to receive the outputs of other electrical circuits, which furnish the stimulating signals.

Methods of manufacturing such array are also disclosed herein. In addition, the methods of connecting to tissue of a living body, utilizing the device of the invention, are disclosed herein.

It is, therefore, an object of this invention to provide an electrode array, for connection to a living body, and having output connections which may be used to select desired electrodes for connection to an electrical circuit.

It is also an object of this invention to provide a penetrating electrode array for connecting electrical circuits to the body.

It is another object of this invention to provide an implantable penetrating electrode array.

It is another object of this invention to provide a penetrating electrode array which provides a high likelihood of successfully making a desired electrical connection with a body part.

Another object of the invention is to provide a penetrating electrode array which minimizes the likelihood of damage to a patient.

A further object of this invention is to provide an orderly electrode array having output connections which may be used to select desired electrodes for connection to an electrical circuit.

A still further object of this invention is to provide a penetrating electrode array which may be attached to one or a plurality of nerve fibers for sensing or stimulating purposes.

Still another object of this invention is to provide methods of manufacturing an electrode array for connecting to tissue of a living body.

A further object of this invention is to provide a method of making electrical connection with living tissue of a body.

Other objects and features will be apparent from the following description together with the drawings in which.

FIG. 12 illustrates a monolithic base structure in which several electronic devices are created and on which are created the protuberances for penetrating the body tissue; and FIG. 13 shows interconnected electronic devices for switching the output of a sensory device. A transmitter and receiver are shown, for transmitting the sensed information and receiving information for controlling the switching of the sensing needles, or protuberances;

FIG. 14 is a partial drawing of a base, having three indexing cones thereon, with a cone from above fitting between them; and FIG. 15 is a side view of the three indexing cones, showing the cone from a mask, cover or other overlying device, fitting between the cones.

DETAILED DESCRIPTION

The electrode array of the invention is applied to body tissue to provide an effective electrical connection therewith, whether for sensing or stimulating purposes. The array of needles provides a multiple possibility of successful electrical contact, and is intended to cause minimal damage to the tissue or upset to the body system. The needles have electrical conductors to terminals which provide for connecting individual needles, or groups of needles, of the electrode array to other electrical circuits.

Such other electrical circuits, in the case of sensing, would likely be, first, amplifiers (because of the low voltages involved in sensed body signals). Then, of course, the signals (information) may go on to be handled by analog or digital electronic methods and may involve transmission, multiplexing, filtering, data processing or other known electronic techniques. The particular use would determine the particular other electrical circuits to be used.

In the case of stimulation, the other circuits which would be connected to the terminals would likely be outputs of circuits which provide the stimulation signals.

Figure 1:
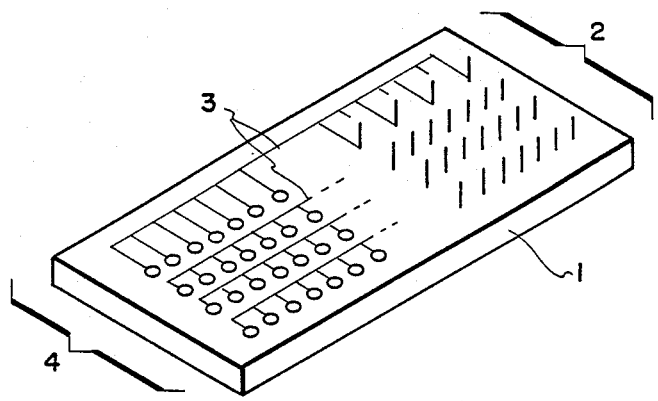
FIG. 1 is a perspective illustrating the concept of "bed of nails," showing the sharp protuberances and terminals. The electrical conductors between the protuberances and the terminals are individual conductors, but are shown combined, for simplicity.

FIG. 1 is a perspective illustrating the concept of "bed of nails," showing the sharp protuberances and terminals. It is so drawn to provide the concept of a base 1 having protuberances, or needles 2 thereon, connected by conductors 3, to terminals 4 (bonding pads, in this case).

Figure 2:
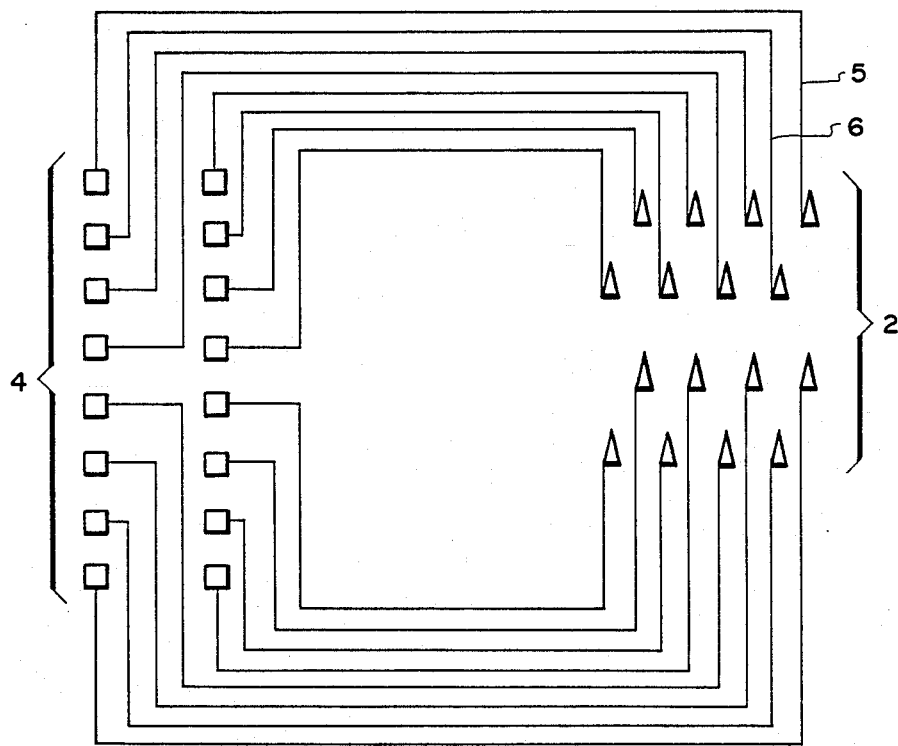
FIG. 2 illustrates the individual conductors from protuberances (needles) to terminals (bonding pads)

FIG. 2 is a more detailed view, illustrating the concept of connecting the needles 2 of an array to terminals, showing the individual conductors, such as 5 and 6.

Figure 3:
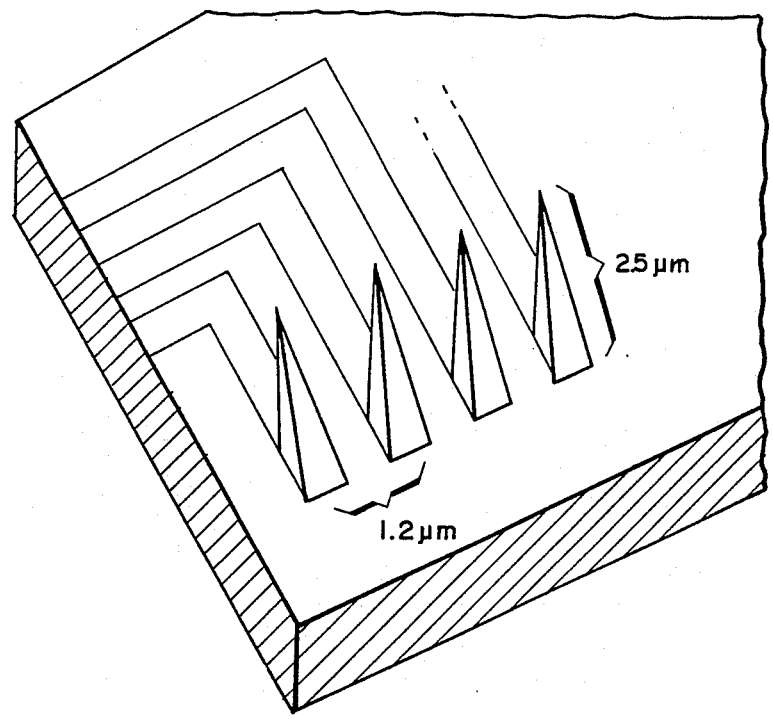
FIG. 3 is a view of an array of protuberances in the shape of pyramids, illustrating the dimensions which may be involved.

FIG. 3 is a view of an array of protuberances in the shape of pyramids, illustrating the dimensions which may be involved. The protuberances, or needles, may, of course, be taller and narrower. Spacing may vary, as may the needle size. Of course, such needles may be conical or other elongated shape.

Figure 4:
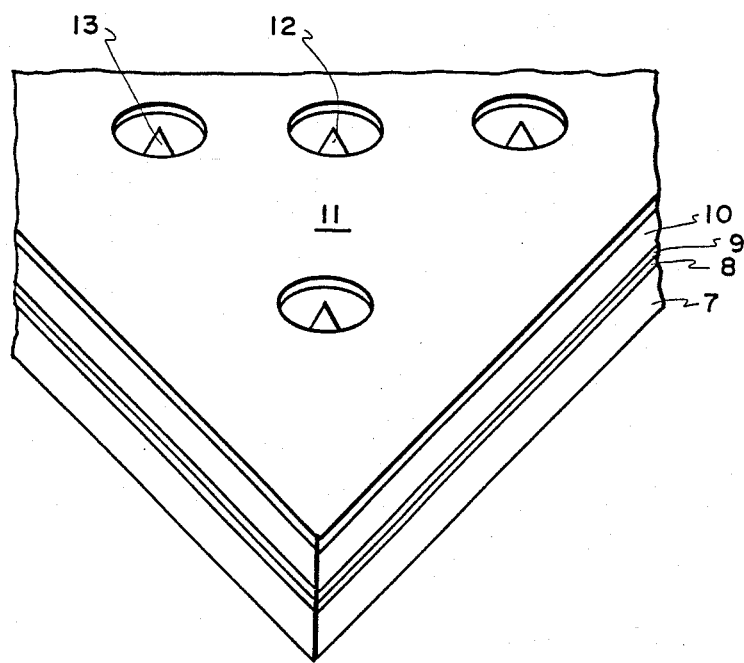
FIG. 4 illustrates protuberances (cones, or needles, in this case) being grown through a mask, on a metallic film on a base, or substrate of silicon.

FIG. 4 illustrates protuberances (cones or needles, in this case) being grown through a mask, on a metallic film on a base, or substrate of silicon. The sandwich shown is a base 7, (say, of silicon), having a silicon dioxide, insulating layer 8 thereon, followed by a metal layer 9 (out of which the conductors are formed and on which the cones are formed). Next, is a spacing dielectric layer 10 (which, in some embodiments and manufacturing processes may not be necessary) which may be of silicon dioxide. Next, is the top mask or fine mesh screen 11. Such screen may be non-conductive although, if it is desired to deposit material on it (to make its holes smaller, for creating smaller cones through the smaller holes), it may be conductive.

Figure 5:
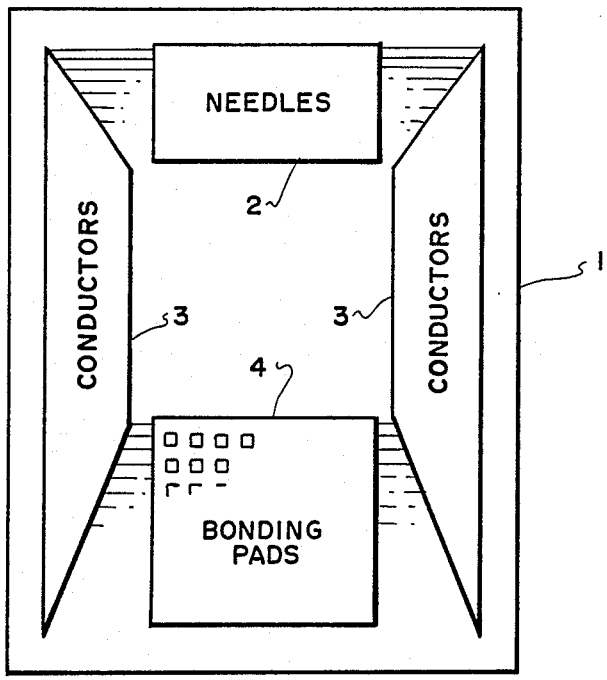
FIG. 5 shows a layout, on a base, of electrical connections and terminals (in this case, bonding pads), showing their connection to the needles.

FIG. 5 shows a layout, on a base 1, of electrical conductors 3 and terminals 4 (in this case, bonding pads), showing their connection to the needles 2.

Figure 6:
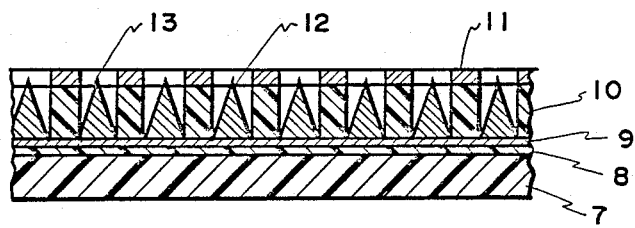
FIG. 6 is a cross-section of a deposition mask, showing the cones deposited through the holes of the mask, with the cones shown deposited on an electrical conductor, or lead, disposed on a dielectric layer on a base.

FIG. 6 is a cross-section of a deposition mask 11, showing the cones deposited through the holes of the mask, with the cones, such as 12 and 13, shown deposited on an electrical conductor, or lead 9. Also shown, are underlying silicon dioxide layer 8 and base, or substrate 7.

Figure 7:
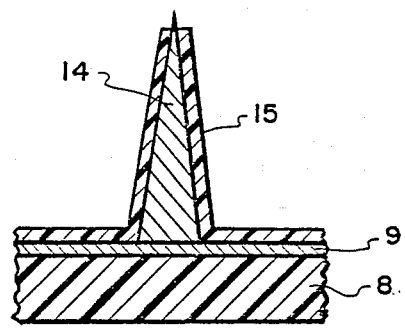
FIG. 7 is a cross-section illustration of a needle covered with a dielectric, or insulating layer, except at its tip.

FIG. 7 is an illustration of a needle 14 covered with a dielectric layer 15 (of silicon dioxide), except at its tip. The metal layer 9, out of which the electrical conductors are formed, is shown. Also shown is dielectric layer 8 (silicon) dioxide). The underlying base is not shown.

Figure 8:
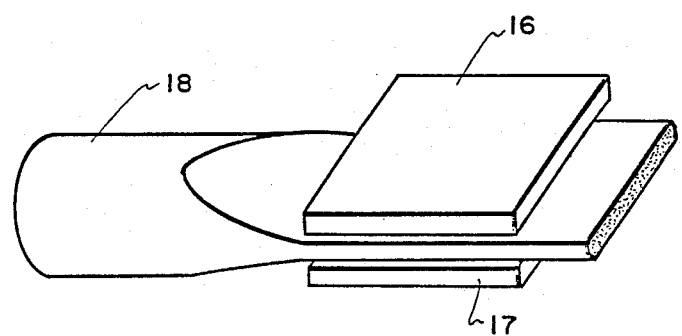
FIG. 8 is an illustration of two electrode arrays disposed on a nerve.

FIG. 8 is an illustration of two electrode arrays 16 and 17 disposed on a nerve 18. The nerve is shown simply flattened although it may be prepared to receive the arrays by removal of a portion, or all of its sheath, or its surrounding structure. The electrode array, particularly, the terminals (bonding pads) portion, may overhang so as to clear the nerve and permit connection to the terminals of the array. It is also desired in some embodiments to provide edge connections for such array in order to more conveniently connect to it.

It may also be seen that such electrode array may be used as an electrode on the skin, such as for an electrocardiograph or electroencephalograph. Of course, the array may be lightly applied or applied so as to penetrate the skin. By penetrating the skin, a better connection is obtained without the use of conductive ointments. In addition, a capacitive coupling may be obtained by having the needles entirely covered with a passivating layer (a dielectric) and applied to penetrate the skin. Thus, the surface areas of the cones become one capacitive plate of substantial area, and the dielectric lies between such plate and the other plate of the capacitor, the body (tissue).

Figure 9:
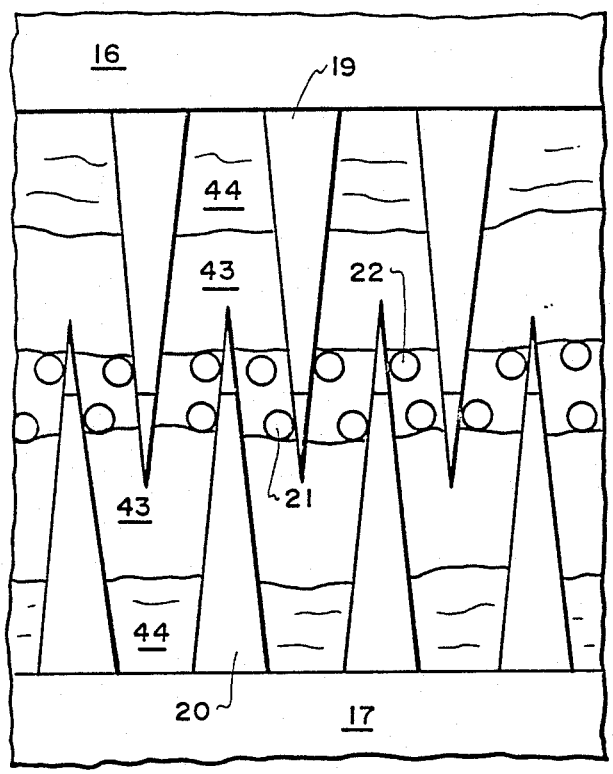
FIG. 9 shows interdigitated needles penetrating a nerve from opposite sides, and contacting nerve fibers.

FIG. 9 is a cross-section of a nerve and shows interdigitated needles, as might occur from the FIG. 8 arrangement. The interdigated needles, such as 19 and 20, are shown penetrating a nerve from opposite sides, and contacting (or in near proximity to) the myelinated or unmyelinated fibers 21 and 22. The needles are shown penetrating the perineurial sheath 43 and the extraperineurial tissue 44. Some of such tissue may be removed in preparation for application of the electrode arrays. It is noted that the needles are shown as exposed only at their ends. Such structure is particularly useful in sensing, in order to limit the sensed electrical activity to a single fiber or a few fibers. A larger portion of the needle may be exposed in stimulating situations. By choosing the correct dimensions, needle length, exposed tip length, amount of interdigitation, and needle spacing, the likelihood of successful contact with single fibers is greatly enhanced.

Figure 10:
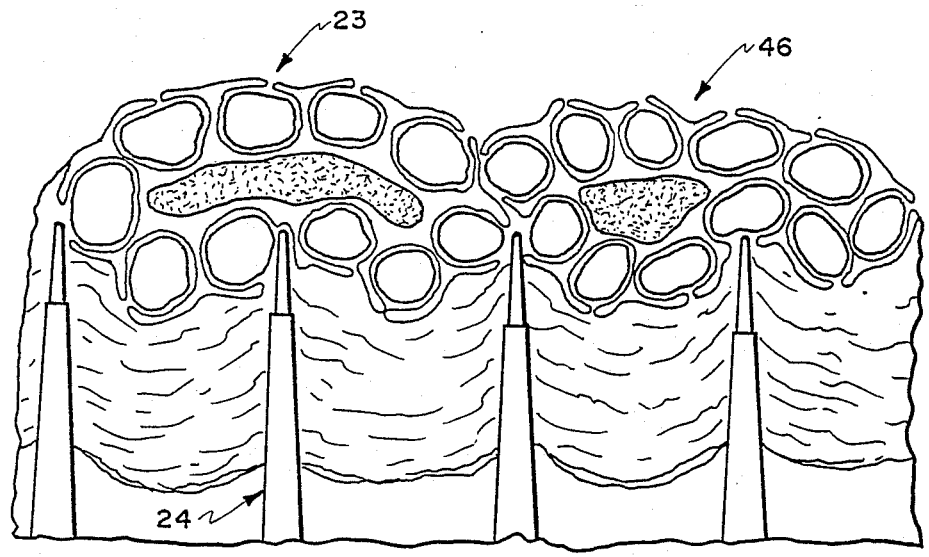
FIG. 10 shows two Schwann cells enveloping myelinated nerve fibers, and a needle in close proximity to the fibers.

FIG. 10 shows Schwann cell structures 23 and 46 disposed around "C" class nerve fibers, such as 25, 47, and 48. A needle 24 is shown in close proximity to nerve fiber 25.

Figure 11:
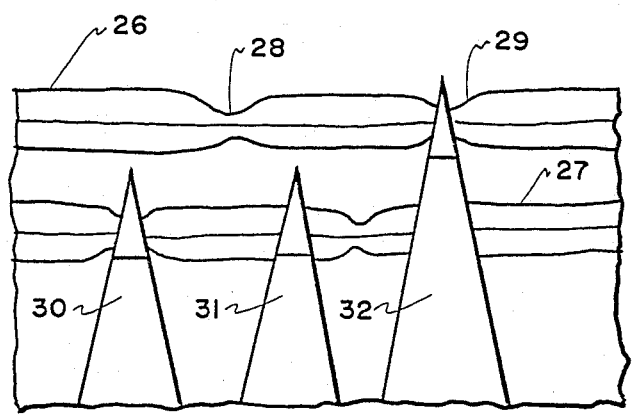
FIG. 11 illustrates two myelinated nerve fibers and their nodes of Ranvier and the protuberances, or needles, in proximity to said nodes.

FIG. 11 shows two nerve fibers 26 and 27, their nodes of Ranvier, as at 28 and 29, and the needles 30, 31 and 32. Needles 30 and 32 are in proximity to said nodes and would more likely pick up electrical signals than would needle 31.

FIG. 12 illustrates a monolithic base structure 33 in which several active electronic devices 34, 35, 36, 37 and 38 are created and on which are created the protuberances 2, for penetrating the body tissue.

FIG. 13 shows the interconnected electronic devices for switching the output of a sensory device. The transmitter and receiver 38 are shown, for transmitting the sensed information and receiving information for controlling the multiplexor 36 and the selective logic 34 of the sensing needles, or protuberances. Logic control 37 provides control over the multiplexor 36 and the selective logic 34. In this manner external control may be exercised in order to select particular needles which are in suitable contact, or proximity, to desired nerve fibers. Amplifiers 35 provide increased signal strength. Integrated circuit technology may be used to provide the desired interconnections. Further, it may be appreciated that the transmitter and receiver 38 may be other than radio frequency. They may transmit and receive utilizing infrared, magnetic induction, reflected impedance, acoustic waves, volumetric conduction or any other suitable well-known means for transmitting and receiving information. In addition, such transmitter and receiver may be powered from outside the body. The entire implanted, electrode array may be powered from outside the body by power transferred into the body through the receiver. In this manner, one or more arrays could be coordinated to operate together, or in response to one another. An array in the brain could, without any wires, (tetherless), communicate and control an array on a muscle, a nerve or other body part. An array, or several arrays, attached to the motor cortex of the brain, could transmit, in tetherless fashion, many channels of information to receiving body parts, such as muscles, (having arrays attached thereto).

FIG. 14 shows an indexing, or alignment means, in which three cones (or pyramids, or conical protuberances) 39, 40 and 41 (viewed from the top), intermesh with a cone 42, (viewed from its bottom and shown crosshatched) from an overlying mask, cover, or other item, needing registration.

FIG. 15 illustrates a side view of the three cones, 39, 40 and 41 and the top cone 42, illustrating how such cones fit together and index, or align, two devices. Two or more of such groups would be used in accomplishing the registration. It is not believed alignment has been achieved, previously, using such microstructures.

A common use of the electrode array would be in connecting to a nerve. A nerve is generally of linear shape, but does not, ordinarily, lie in a straight line. Considering the needles of the array to be longitudinally disposed along the direction of the nerve, one or more needles along such longitudinal direction may make contact with the same or different nerve fibers. The needles most likely to be useful are those which touch, or are in close proximity to, the desired fibers. Laterally-spaced needles may also be found to have made contact with the same nerve fiber. Other laterally-spaced needles may connect to nearby nerve fibers, which may have the same or different signals. Reinforcement of the sensing of signals can thus be obtained. Similarly, reinforcement of stimulation signals can thus be provided. From the explanation provided above, it can be seen that sensing or stimulation of the same or different nerve fibers is possible.

The smallest class of nerve fibers, are unmyelinated "C" fibers. Adjacent fibers of this class appear (from our own observation) to be spaced from approximately ½ micrometer to 5 micrometers apart, center to center. Larger nerve fibers, ("A and B fibers"), which are usually myelinated (surrounded by a sheath), appear to be spaced approximately 10 micrometers to 50 micrometers, from adjacent fibers. In addition, a thickness of connective tissue encloses all of the component fibers in a nerve. In order to penetrate the nerve, or in order to enter the fiber bundle, sufficiently, but not too much, the needles would be approximately ½ micrometer high to on the order of 100 micrometers high. In selecting the correct needle height, consideration has to be given to the sheaths, Schwann cells, and other tissue, to be penetrated in order to contact the nerve fiber. Similarly, for other tissue, the depth of penetration desired would determine the height of the needles. If the needles are fabricated with optimal materials and geometrics within the above-described dimensions, emphasizing a small tip radius, narrow taper, spacing and length appropriate to the tissue involved, the likelihood of making electrical contact, with a minimum of tissue damage, is high.

Depending on the capability of creating long needles, it is desired to have them as long and narrow as possible. Aspect ratios (height to base) of 10 to 1 are readily achievable. A needle which is 100 micrometers high might have a base of from 5 micrometers to 10 micrometers in diameter or greater.

It may be appreciated that the small size of the needles minimizes the likelihood that nerves, organs, tissue, or other body part would be damaged by application of the array and penetration by the needles.

The spacing of the needles, transversely across a nerve, would be from approximately ½ micron to on the order of 100 micrometers. "On the order of" means, in this context, and as used herein, within the range of 1/10 of the dimension to 10 times the dimension. Spacing of the needles along the length of a nerve, might well be different—greater, than spacing of the needles laterally, across the nerve. That is, the spacing distance between needles along the length of a nerve can vary a great deal. Needles, or groups of needles, might well be spaced apart 1000 micrometers, 2000 micrometers, etc., longitudinally, depending on the desired density of electrical contact with the nerve.

The needles (electrodes) must, therefore, be spaced having in mind the specific application. The needles necessarily must be small and sharp enough to not only avoid damaging the nerve, but also, the electrically-conductive portion of each needle should be small enough to contact only a single fiber and thereby obtain signals from only one fiber. Consequently, a preferred embodiment of the invention is to insulate the needles, except at, or near, their tips so that only a small electrically-conductive portion of each needle is exposed. In this way, each needle is less likely to electrically contact more than one fiber.

In addition, the needles must be high, or long, enough to assure sufficient penetration of the desired nerve so as to make electrical connection with the nerve fiber, inside the nerve. In order to reach the nerve fiber, the sheath and other connective tissue must be penetrated. However, "electrical connection" or "contact" with a nerve fiber, or other body tissue may mean actual physical contact with the nerve fiber, or tissue, or it may mean, being in sufficiently close location to sense the electrical signals from, or to stimulate, the fiber or tissue, as discussed previously in connection with FIG. 11. Further, as discussed previously, if the needles are entirely covered with a dielectric and utilizing capacitive coupling, the conductive part of the needles do not actually touch body tissue.

If the longitudinal direction of the array is slightly canted with respect to a nerve, electrical contact with some of the needles with some of the nerve fibers can be assured.

The spacing and needle length may vary on a given base. In order to reach down into a fissure, in the brain, for example, it may be desired to have the needles on that portion of the array longer than elsewhere on the array, or to have a greater or lesser density (lesser or greater spacing between needles, respectively), than elsewhere on the array. There may be, of course, an abrupt change of needle length or density, or both, in one or more directions. Or there may be a graded, or gradual, change in one or more directions.

It is to be understood that the array may be sized to fit the particular application and may be planar, multiplanar, curved, twisted, or other desired shape, as required in the particular circumstances involved. Ordinarily, the needles of the array would be disposed on a rigid base, however, it is to be appreciated that the base may be flexible, or that the electrode array may be comprised of needles on a plurality of bases. In general, the needles in an array would be held in relatively-fixed spacing with respect to each other. It is intended to cover by "relatively-fixed" terminology, instances in which the base is flexible, curved, stretchable, etc. Among the suitable bases are silicon, sapphire, or germanium. Numerous ceramics are also suitable for such biomedical use. Biomedical grade plastics may also be used such as the polyamides, polymethacrylate, acrylics, polycarbonates, etc., to the extent such plastics may be implantable or rendered implantable.

The needles may be arranged in random fashion, or ordered in columns, or rows, or columns and rows or other ordered arrangement. The optimum embodiment from the standpoint of orderly electrical connection is an ordered arrangement. One embodiment which may be desired is that in which each electrode (except, of course, those near the edges of the array) is surrounded by six other electrodes, all equidistantly spaced. The needles are electrically connected to terminals (which may be bonding pads, for connection to other electrical circuits) which may, likewise, be randomly located or located in columns, or rows, or columns and rows. Connection points need not be in the same arrangement as the needles. Thus, the needles may be located in columns, but not rows, and the terminals may be located in columns and rows.

It may be understood that the array, as described herein, provides a greater likelihood than the prior art, of successfully contacting a desired nerve fiber or desired location in a part of the brain, or other part of the body. Through testing and selection of appropriate terminals, the needles which make the successful contact desired in the body, can be connected to output equipment (for sensing purposes) or input equipment (for stimulation purposes).

The needles (sharp protuberances) may be constructed as "cones", and a method of construction may use techniques similar to those taught in U.S. Pat. Nos. 3,755,704, 3,789,471 and 3,812,559, inventors, Charles A. Spindt et al. Art prior to those references include U.S. Pat. No. 3,453,478, inventors, Kenneth R. Soulders and Louis N. Heynick. Of course, it is not essential that the needles be "cones", but may be of pyramidal shape or shaped as any sharp protuberance. Further information on the fabrication technology involved, may be found in an article by C. A. Spindt and others, entitled "Physical properties of thin-film field emission cathodes with molybdenum cones," Journal of Applied Physics, Vol. 47, No. 12, December, 1976. In those patents and the article, the intended use of the structure and method is to provide field emission cathodes and field ionizers. Such needles, as disclosed by Spindt, contemplate electron-emitting structures as may be utilized in a vacuum tube. Also, he contemplates an electric field of megavolts per centimeter and current density of millions of amperes per square centimeter. For electron emission, contemplated voltages are of the order of kilovolts and for field ionization, approximately tenfold higher. See Col. 2, l. 3 et seq., U.S. Pat. No. 3,812,559.

The device of the invention, on the other hand, as either a sensor or a stimulator, is concerned with very low electrical currents and voltages. The needles of the electrode array of this invention would, ordinarily, not be connected in common, but each needle would provide its individual output, although it is to be understood that groups of needles could be connected together, to provide a common, or reinforced output, of either stimulation or sensing. Further, in a particular situation, all needles of an array could be connected together to provide a single stimulating output or a single sensing output.

In one contemplated method of manufacture, a common base (substrate) is used in order to mount the needles and to achieve desired deposition. The base may have to be modified to provide the desired isolation of the individual needles or needle groupings. Such original base, as modified, may provide the necessary electrical conductors to convenient terminals or bonding pads, (for connecting to other electrical circuits).

The various steps of manufacture of the electrical conductors and terminals (bonding pads) may be accomplished by known techniques of chemical or electrical plating, etching, diffusing, sputtering, evaporation or other suitable techniques. This may be accomplished by using photolithographic or photographic techniques, masks, photoresist, etchants and associated materials, known to those skilled in the microcircuit art.

A suitable mask may be generated by a drawing, followed by a photograph of the drawing, the making of a negative or positive, covering a mask material with a photoresist, exposing the photoresist through the negative or positive, developing it and etching to generate the mask. Fine mesh screens may be readily purchased or a mask may be created as described above, or by other known techniques.

In one embodiment, the steps of manufacture are,

1. A non-conductive substrate, say, silicon, having a silicon dioxide layer formed thereon is used. A foil or film of conductive material is affixed thereon, (possibly, by sputtering, evaporation or other known integrated circuit manufacturing technology);

2. Using a photoresist and a suitable mask, a pattern of electrical conductors and terminals (bonding pads) is laid out on the conductive material and all the rest of the material is etched or removed. It would be possible to commence with a non-conducting substrate, and, using known chemical deposition techniques, lay down a sensitizer in the form of the desired conductive pattern, which would allow subsequent chemical deposition of a conductive metal as the electrical conductors and terminals;

3. After cleaning the article, a glass passivation layer is laid down on the electrical conductors and terminals;

4. Again, using a photoresist, a suitable mask (defining the needle sites) and an etchant are used in order to locate the needle sites and to etch through the glass passivating layer, exposing each of the sites for growing a needle on an electrical conductor of the layer below;

5. The same mask or a similar mask having holes therethrough, at the desired needle sites is disposed over the exposed needle sites in registration with such sites, and deposition of the needles is accomplished through such mask by metallic evaporation (using, for example, electron beam or resistive element heating) in a high vacuum chamber. The metal deposits on the mask as well as within the hole, on the needle site. The mask hole slowly closes and a needle cone is formed as the hole closes. The evaporating metal used to form the cones (needles) may be platinum, activated iridium, platinum iridium alloy, possibly, rhenium, or other suitable, implantable electrode material. It is desired that the cones be made of a conductor which can deliver stimulus current, (if stimulating), or sense very small voltages, (if sensing), with little or no corrosion. If the mask is a fine mesh screen through which the needles are deposited, the precise size of the holes required for creating the needles may be obtained by placing the mask (covering the device) in a vacuum deposition system and rotating the device about an axis vertical to its surface and depositing, at a grazing incidence, more metal on the screen or mask layer. This can be used to decrease the starting size of the holes to any diameter. Upon arriving at the desired diameter, the needles may be created by orthogonally plating through such narrowed holes as taught in U.S. Pat. No. 3,812,550, referred to above;

6. The mask through which deposition is accomplished, is carefully removed, leaving the needles exposed, providing the "bed of nails";

7. A photoresist, a mask having the pattern of the test points and terminals, and an etchant are used to remove the passivating layer over the test points and terminals in order that connection can be made to the array; and 8. Ordinarily, it would be desired to have only a small portion of the tips (say, 1 or 2 micrometers) of the needles conductive. In such cases, the array of needles may be covered with a passivating layer, such as of glass, and the tips of the needles are exposed by etching. Other methods may be used to cover all but the tips of the needles.

The above process utilizes various of the manufacturing steps disclosed in the above-mentioned Journal of Applied Physics article, and in the above-mentioned patents.

The manufacturing operation may commence with a thin film sandwich of metal on a dielectric (probably, silicon dioxide) on a base of silicon. The conductive and terminal pattern is formed out of the metal layer, by etching away excess metal. Then, using a mask for needle sites, the needles are grown on the conductive pattern, as desired. After the needles have been formed, the entire device could be covered with a glass passivating coat except the needle tips and terminals, if they are desired to be left exposed. They could, of course, be exposed later, as desired.

In another method, a thin film sandwich is used, having a bottom layer of dielectric, a next layer of metal, then a dielectric and then metal on top of that. The top layer of metal becomes the mask for creating the needles. The thickness of the bottom dielectric layer is determined by what rigidity and strength is necessary in order to hold on to and carry the electrode array. The second dielectric thickness is determined by the spacing desired between the top metal layer (which will form the mask for the needle growing) and the middle metal layer upon which the needles will be grown. A very thin, second dielectric layer may be created between the metal layers by the use of evaporated silicon dioxide. The under layer of metal will form the needle sites, the electrical conductors, test points, if any, and terminals, (bonding pads, in one embodiment). The top layer of metal is used as a mask for depositing the needle cones on the under layer of metal. This is accomplished by first making holes in the top layer of metal, at intended needle sites, without penetrating the dielectric between the metal layers. This is done by a selective metal etchant (together with a photoresist and a mask) which does not attack the dielectric. Then an etchant is used to remove the dielectric between the metal layers, at the needle sites. The needles are then "grown", by vacuum evaporation, sputtering or other known techniques. After having formed the needles on the metal layer on the bottom dielectric layer, all of the second dielectric layer and top metal layer would be removed. The excess metal (not needed for electrical conductors, test points and terminals) of the exposed under layer metal could then be removed. In the alternative, the entire under layer metal could be removed and new metal, making electrical conductors between the needles and terminals could be deposited. The entire electrode array could then be covered with a passivating material (such as silicon dioxide, silicon nitride, $Al_2O_3$ or other biocompatible dielectric) and then selectively etched at the terminals, if desired, and at the needle points.

If the substrate is silicon or germanium or the like, the electrical conductors, and, if desired, switches, multiplexors, amplifiers and other electronic circuits may be provided by doping selected portions of the substrate or by other commonly-used techniques. Doping may be accomplished before the growing of the needles. Electrical conductors may be created on the surface of the semiconductor material, in it, or through it, to the opposite side from the protuberances.

In obtaining registration, or indexing, of masks, covers, or other items, which must be aligned with the array, one or more groups of three cones, or needles, could be grown in two or more places on the array and a registering cone, or needle, grown on the other item to be aligned. A needle on the overlying device fits into the space within the group on the other device, as previously described in connection with FIGS. 14 and 15. Of course, the overlying device may have the groups of needles, and the base have the single registering needles. Further, both devices may have a group which fits into a group on the other device.

The materials used in the structure, must be biocompatible and suitable for use in, or in connection with, the living body. It is understood, of course, that certain materials which are not considered biocompatible could be rendered suitable by being treated or covered with a biocompatible material. Thus, glass passivation, (covering with glass), oxidation of certain materials, the coating or depositing of biocompatible materials, (such as, but not limited to, silicone rubber, certain metals and ceramics, or one of the many plastics which are used in the body), may be used to provide a final product which is biocompatible and may be implanted. The electrode or needle material may be platinum, activated iridium, a platinum iridium alloy, a conductive polymer, carbon or other suitable electrically conductive material known by those skilled in the art as suitable for use in connection with the body. In general, metals or other conductive substances which are inert and are least subject to corrosion, are used. In the case of stimulating devices, metals which can handle the necessary current densities are required.

In view of the above discussion, it may be understood that the electrode array would be useful in stimulating a gland, or a nerve to or in the gland, to cause the gland to be active or more active. The electrode array may be used to cause hormonal secretions.

Other uses of a stimulating electrode array or a plurality of electrode arrays, would include stimulation of a group of muscles or successive stimulation of groups or portions of a group to achieve a desired muscular coordination. Such electrode array may be applied directly to or in the muscle or it may be applied to or in selected nerves (or the central or peripheral nervous system) to provide signals to the muscle. Also, a number of such arrays may be applied at different locations and their stimulation (or sensing) coordinated to achieve desired results.

One stimulation application of the array, or a plurality of such arrays, is in excitation of the brain to provide a sensory response, for example, vision. The array, and its numerous needles, may be disposed, say, in the visuosensory and visuopsychic areas of the brain, which involve several kinds of cells. The array may be disposed along the optic nerve or the paths where the optic nerve enters the cortex. The array may be attached to the cortex, with the needles penetrating the brain rather than the optic nerve.

The concept of the invention, in one of its more important aspects, provides for electrical access to the individual elements of a tissue in order to determine which element or elements and its associated needle, or needles, are useful for the intended purpose. One or more needle outputs may be found to be useful in the particular application involved.

It is also be appreciated that, as taught hereinabove, the device may be untethered, through one or more means for transmitting information, receiving information or receiving power.

Although the invention has been described and illustrated in detail, it is to be clearly understood that the same is by way of illustration and example only and is not to be taken by way of limitation, the spirit and scope of this invention being limited only by the terms of the appended claims.

We claim:

1. A method for making an electrode array comprising the following steps:
   step (a): obtaining a base with a non-conductive surface, then
   step (b): depositing a layer of electrically conductive material atop the non-conductive surface, and
   step (c): defining sites upon the layer of electrically conductive material for an array of protuberances, and then
   step (d): depositing electrically conductive protuberances upon the sites for the array, the protuberances having tips, and
   step (e): forming conductors for electrically connecting to the protuberances by partially removing the layer of electrically conductive material, and then
   step (f): depositing a dielectric coat upon the protuberances, exclusive of the tips.

2. A method for making a capacitive electrode array comprising the following steps:
   step (a): obtaining a base with a non-conductive surface, then
   step (b): depositing a layer of electrically conductive material atop the non-conductive surface, and
   step (c): defining sites upon the layer of electrically conductive material for an array of protuberances, and then
   step (d): depositing electrically conductive protuberances upon the sites for the array of protuberances, the protuberances having tips, and
   step (e): forming conductors for electrically connecting to the protuberances by partially removing the layer of electrically conductive material, and then
   step (f): depositing a dielectric coat upon the protuberances.

* * * * *